United States Patent [19]

Yamato et al.

[11] 4,226,779
[45] Oct. 7, 1980

[54] PROCESS FOR ISOMERIZING METHYL-DELTA-4-TETRAHYDROPHTHALIC ANHYDRIDE

[75] Inventors: Motoyuki Yamato, Kamakura; Tadao Natsuume, Yokosuka, both of Japan

[73] Assignee: Nippon Zeon Co. Ltd., Tokyo, Japan

[21] Appl. No.: 34,502

[22] Filed: Apr. 30, 1979

[30] Foreign Application Priority Data

May 4, 1978 [JP] Japan .................................. 53-52670
Jun. 2, 1978 [JP] Japan .................................. 53-66533

[51] Int. Cl.$^2$ ............................................. C07D 307/89
[52] U.S. Cl. ................................................... 260/346.3
[58] Field of Search ..................................... 260/346.3

[56] References Cited

U.S. PATENT DOCUMENTS

| | | | |
|---|---|---|---|
| B 392,798 | 3/1976 | Corson | 260/346.3 |
| 2,764,597 | 9/1956 | Barney | 260/346.3 |
| 2,959,599 | 11/1960 | Bailey | 260/346.3 |
| 3,470,214 | 9/1969 | Young | 260/346.3 |

OTHER PUBLICATIONS

Craig, Journal of the American Chemical Society, vol. 72, (1950), pp. 1678–1681.

*Primary Examiner*—Richard Raymond
*Attorney, Agent, or Firm*—Sherman & Shalloway

[57] ABSTRACT

A process for isomerizing methyl-delta-4-tetrahydrophthalic anhydride, which comprises heat-treating it at 60° to 300° C. for 0.1 to 30 hours in the presence of at least one nitrogen-containing compound selected from the group consisting of (a) a quaternary ammonium compound and (b) a compound having a nitrogen atom bonded to the carbon atom of the carbonyl group (e.g., an amide, imide, carbamate, urea or semicarbazide compound). The product is liquid at room temperature, and especially suitable for use as a curing agent for epoxy resins.

5 Claims, No Drawings

PROCESS FOR ISOMERIZING METHYL-DELTA-4-TETRAHYDROPHTHALIC ANHYDRIDE

This invention relates to a process for isomerizing methyl-delta-4-tetrahydrophthalic anhydride. More specifically, this invention is concerned with a new process for isomerizing methyl-delta-4-tetrahydrophthalic anhydride which comprises heat-treating it in the presence of a specified nitrogen-containing compound.

Methyl-delta-4-tetrahydrophthalic anhydride (to be abbreviated "Me-$\Delta^4$-THPA" hereinbelow) has been used widely as a curing agent for epoxy resins or as a component of unsaturated polyester resins. However, the fact that this compound is solid at room temperature is a great defect in using it as a curing agent for epoxy resins which is frequently required to be liquid for the ease of handling.

Methods have been developed heretofore to obtain liquid Me-$\Delta^4$-THPA by isomerization. Known methods include, for example, the heat-treatment of Me-$\Delta^4$-THPA using a catalyst such as palladium or ruthenium (U.S. Pat. No. 2,764,597), sulfuric acid, phosphoric acid, etc. (U.S. Pat. No. 2,959,599), and silica-alumina or acid-type ion exchange resins (U.S. Pat. No. 3,470,214). According to these methods, the position of the double bond of the cyclohexene ring is shifted to form structural isomers, and the melting point of the product is lowered by forming a eutectic mixture of these structural isomers.

A method is also known which effects the steric geometric isomerization of Me-$\Delta^4$-THPA without inducing the shifting of its double bond. For example, Journal of American Chemical Society, Vol. 72, pages 1678–1681 (April, 1950) reports that 3-Me-$\Delta^4$-THPA has four geometric isomers, i.e. cis-3-methyl-4-cyclohexene-cis,cis-1,2-dicarboxylic anhydride (m.p. 63° C.), trans-3-methyl-4-cyclohexene-cis,cis-1,2-dicarboxylic anhydride (m.p. 41° C.), cis-3-methyl-4-cyclohexene-cis,trans-1,2-dicarboxylic anhydride (m.p. 133° C.) and trans-3-methyl-4-cyclohexene-cis, trans-1,2-dicarboxylic anhydride (m.p. 121° C.), and that heat-treatment of the cis-3-methyl-4-cyclohexene-cis,cis-1,2-dicarboxylic anhydride having a melting point of 63° C. at 175° C. for 4 hours in the presence of dibutyl aniline gives an isomeric mixture having a melting point of 30° C. However, no report has been published which describes the successful preparation of a liquid product by geometric isomerization, and information has been scarce on catalysts which may be used in this reaction.

It is a primary object of this invention to provide a process which can afford a liquid isomeric mixture of Me-$\Delta^4$-THPA as a result of discovering a novel isomerization catalyst.

The object of this invention is achieved by a process for isomerizing methyl-delta-4-tetrahydrophthalic anhydride, which comprises heat-treating it in the presence of at least one nitrogen-containing compound selected from (A) a quaternary ammonium compound and (b) a compound having a nitrogen atom bonded to the carbon atom of the carbonyl group.

Me-$\Delta^4$-THPA used in this invention is 3-Me-$\Delta^4$-THPA, or 4-Me-$\Delta^4$-THPA or a mixture of these. These compounds can be easily obtained, for example, by subjecting 1,3-pentadiene, isoprene or both, and maleic anhydride to a Diels-Alder reaction. 3-Me-$\Delta^4$-THPA is more susceptible to isomerization than 4-Me-$\Delta^4$-THPA.

To obtain a product which is liquid at 20° C., it is advantageous to use 100 to 20% by weight, preferably 95 to 25% by weight, of 3-Me-$\Delta^4$-THPA and 0 to 80% by weight, preferably 5 to 75% by weight, of 4-Me-$\Delta^4$-THPA.

In the present invention, Me-$\Delta^4$-THPA is heat-treated in the presence of the specified nitrogen-containing compound to induce its isomerization.

The quaternary ammonium compound (a) denotes ammonium salts, ammonium hydroxides, or nitrogen-containing compounds resulting from substituting organic groups for some or all of the hydrogen atoms bonded to the nitrogen atom of the aforesaid compounds. Specific examples include ammonium compounds such as ammonium chloride, ammonium sulfate, ammonium nitrate and ammonium hydroxide; primary, secondary or tertiary amine salts such as monoethylamine hydrochloride, diethylamine hydrochloride, aniline hydrochloride, triethylamine hydrochloride, triethylamine perchlorate and triethylamine acetate; quaternary ammonium salts such as tetramethylammonium chloride, tetraethylammonium chloride and triethylbenzylammonium chloride; and quaternary ammonium hydroxides such as tetramethyl ammonium hydroxide, tetraethyl ammonium hydroxide and triethylbenzyl ammonium hydroxide.

These compounds can be used irrespective of the size of the organic groups bonded to the nitrogen atom. For example, strong base-type ion exchange resins and cationic surface active agents which contain the structure of quaternary ammonium salt in the molecules can also be used. From the standpoint of the activity of the catalyst, the quaternary ammonium salts and quaternary ammonium hydroxides are preferred.

The compound (b) having a nitrogen atom bonded to the carbon atom of the carbonyl group denotes compounds which contain in the molecules such a bond as an amide bond, imide bond, urethane bond, urea bond, biuret bond or allophanate bond. Specific examples include amides or the derivatives thereof such as formamide, acetamide, propionamide, butyramide, valeramide, benzamide, N-ethylacetamide, N,N-dimethylformamide, N,N-dimethylacetamide, N-methylbenzamide, N-phenylacetamide, N-phenylpropionamide, ε-caprolactam and γ-butyrolactam; imides or the derivatives thereof such as acetylimide, maleimide, succinimide, phthalimide, tetrahydrophthalimide, methyltetrahydrophthalimide and N-butyl-methyltetrahydrophthalimide; carbamic esters or the derivatives thereof such as methyl carbamate, ethyl carbamate and phenyl carbamate; urea or its derivatives such as urea, N-methylurea, N-ethylurea, N,N'-dimethylurea, N,N-dimethylurea, N,N,N'-trimethylurea, N,N,N',N'-tetramethylurea, N-phenylurea, N,N'-ethylideneurea, N-acetylurea, N-acetyl-N'-methylurea, biuret, N-methylbiuret, N-ethylbiuret, N-benzoyl biuret, methyl allophanate, propyl allophanate and isoamyl allophanate; and semicarbazide or the derivatives thereof such as semicarbazide, 1-acetyl semicarbazide, 1-phenyl semicarbazide and 4-phenyl semicarbazide.

Compounds which react with Me-$\Delta^4$-THPA in the reaction system to form these nitrogen-containing compounds, such as ammonia, primary or secondary amines and isocyanate compounds, can also be used in this invention.

In the present invention, the reaction is carried out at 60° to 300° C., preferably 80° to 250° C., in the presence of usually 0.001 to 5 parts by weight, preferably 0.01 to 2 parts by weight, per 100 parts by weight of Me-$\Delta^4$-THPA, of the catalyst. As the reaction temperature decreases, the rate of isomerization decreases, and with increasing reaction temperature, the coloration of the product increases. The other reaction conditions are not particularly limited. It is adequate to carry out the reaction in an atmosphere of a gas inert to the reaction, such as nitrogen or argon, for a period of about 0.1 to 30 hours, preferably about 1 to 10 hours.

According to the process of this invention, an isomeric mixture having a superior color hue expressed by a Gardner color number of 2 or less can be obtained without distilling the reaction product, if one properly chooses reaction conditions such as the amount of the catalyst, the reaction temperature or the reaction time. The reaction product may be distilled when it is desired to remove coloration which may be caused to some extent, or to obtain a clearer product. By properly controlling the composition of the starting Me-$\Delta^4$-THPA in addition to the proper selection of the reaction conditions as described above, isomeric mixtures which are liquid at 20° C., and those which are liquid even at 0° C., can be obtained. When a mixture consisting of 70 to 50% by weight of 3-Me-$\Delta^4$-THPA and 30 to 50% by weight of 4-Me-$\Delta^4$-THPA is used, an isomeric mixture which is liquid even at $-20°$ C. can be obtained.

The resulting isomeric mixture can be used as a component of unsaturated polyesters, and is also very useful as a curing agent for epoxy resins.

The following Examples illustrate the present invention more specifically. All parts in these examples are by weight.

EXAMPLE 1

A 500 ml. separable flask equipped with a stirrer was charged with 100 parts of 3-Me-$\Delta^4$-THPA having a melting point of 61° C. and a Gardner color number of less than 1 and 0.05 part of tetraethylammonium chloride, and they were reacted in an atmosphere of nitrogen at 200° C. for 3 hours. The resulting product had a Gardner color number of 1 despite the fact that the product was not distilled. The melting point of the product was 10° C.

Nuclear magnetic resonance spectroscopy showed that this product had the following composition:
cis-3-methyl-4-cyclohexene-cis,cis-1,2-dicarboxylic anhydride: about 27%
trans-3-methyl-4-cyclohexene-cis,cis-1,2-dicarboxylic anhydride: about 64%
cis-3-methyl-4-cyclohexene-cis,trans-1,2-dicarboxylic anhydride: about 2%
trans-3-methyl-4-cyclohexene-cis,trans-1,2-dicarboxylic anhydride: about 7%
and that no shifting of the double bond of the cyclohexene ring occurred.

When the above treatment was carried out in the absence of the catalyst, the resulting product had a melting point of 46° C.

EXAMPLE 2

Example 1 was repeated except that 4-Me-$\Delta^4$-THPA having a melting point of 64° C. and a Gardner color number of less than 1 was used instead of 3-Me-$\Delta^4$-THPA. A product having a Gardner color number of 1 and a melting point of 59° C. was obtained.

For comparison, the above reaction was carried out in the absence of the catalyst. The resulting product has a melting point of 64° C.

EXAMPLE 3

Example 1 was repeated using 3-Me-$\Delta^4$-THPA, 4-Me-$\Delta^4$-THPA and each of the various quaternary ammonium compounds indicated in Table 1 in the proportions shown in Table 1. The properties of the resulting products are shown in Table 1.

TABLE 1

| Run No. | 1 | 2 | 3 | 4 | 5 | 6 |
|---|---|---|---|---|---|---|
| Amounts (parts) charged | | | | | | |
| 3-Me-$\Delta^4$-THPA | 80 | 60 | 40 | 20 | 60 | 60 |
| 4-Me-$\Delta^4$-THPA | 20 | 40 | 60 | 80 | 40 | 40 |
| Tetraethyl ammonium chloride | 0.05 | 0.05 | 0.05 | 0.05 | — | — |
| Triethylbenzyl ammonium chloride | — | — | — | — | 0.05 | — |
| Tetraethyl ammonium hydroxide | — | — | — | — | — | 0.05 |
| Properties | | | | | | |
| Melting point (°C.) | 0 | $-20>$ | 0 | 10 | $-20>$ | $-20>$ |
| Color number (Gardner) | 1 | 1 | 1 | 1 | 1 | 1 |

The results given in Table 1 show that all of these quaternary ammonium compounds exhibited good catalytic activity, and that the use of a mixture of 3-Me-$\Delta^4$-THPA and 4-Me-$\Delta^4$-THPA gave a product having a lower melting point.

EXAMPLE 4

Sixty parts of 3-Me-$\Delta^4$-THPA, 40 parts of 4-Me-$\Delta^4$-THPA and a predetermined amount of tetraethylammonium chloride were charged, and reacted under the reaction conditions shown in Table 2. The results are also shown in Table 2.

Table 2

| Run No. | 1 | 2 | 3 | 4 |
|---|---|---|---|---|
| Reaction conditions | | | | |
| Amount of the catalyst (parts) | 0.05 | 0.1 | 0.5 | 1 |
| Reaction temperature (°C.) | 200 | 150 | 100 | 100 |
| Reaction time (hours) | 4 | 4 | 10 | 6 |
| Properties | | | | |
| Melting point (°C.) | $-20>$ | $-20>$ | $-20>$ | $-20>$ |
| Gardner color number | 1 | 2 | 2 | 2 |

The results given in Table 2 show that by properly controlling the reaction conditions, it is possible to obtain isomeric mixtures which are liquid even at $-20°$ C.

EXAMPLE 5

A 500 ml. separable flask equipped with a stirrer was charged with 100 parts of 3-Me-$\Delta^4$-THPA having a melting point of 61° C. and a Gardner color number of less than 1 and 0.1 part of N,N-dimethylformamide, and they were reacted in an atmosphere of nitrogen at 200° C. for 3 hours. The resulting product had a Gardner color number of 1 in spite of the fact that it was not distilled. The melting point of the product was 10° C.

Nuclear magnetic resonance spectroscopy of this product showed that no shift of the double bond of the cyclohexene ring occurred, and similar geometric isomers to those in Example 1 were formed.

When the same treatment as above was performed in the absence of the catalyst, the resulting product had a melting point of 46° C.

EXAMPLE 6

Example 1 was repeated except that 4-Me-$\Delta^4$-THPA having a melting point of 64° C. and a Gardner color number of less than 1 was used instead of 3-Me-$\Delta^4$-THPA. A product having a Gardner color number of 1 and a melting point of 59° C. was obtained.

For comparison, the above reaction was carried out in the absence of the catalyst. The product obtained had a melting point of 64° C.

EXAMPLE 7

Example 5 was repeated using 3-Me-$\Delta^4$-THPA, 4-Me-$\Delta^4$-THPA and each of the various nitrogen-containing compounds indicated in Table 3 in the proportions shown in Table 3. The properties of the resulting products are shown in Table 3.

Table 3

| Run No. | 1 | 2 | 3 | 4 | 5 | 6 | 7 |
|---|---|---|---|---|---|---|---|
| Amount (parts) charged | | | | | | | |
| 3-Me-$\Delta^4$-THPA | 80 | 60 | 40 | 20 | 60 | 60 | 60 |
| 4-Me-$\Delta^4$-THPA | 20 | 40 | 60 | 80 | 40 | 40 | 40 |
| N,N-dimethyl-formamide | 0.1 | 0.1 | 0.1 | 0.1 | — | — | — |
| Phthalimide | — | — | — | — | 0.1 | — | — |
| Tetramethyl-urea | — | — | — | — | — | 0.1 | — |
| N-methylbiuret | — | — | — | — | — | — | 0.1 |
| Properties | | | | | | | |
| Melting point (°C.) | 0 | −20> | 0 | 10 | −20> | −20> | −20> |
| Gardner color number | 1 | 1 | 1 | 1 | 1 | 1 | 1 |

It is seen from the results obtained that all of the nitrogen compounds having a nitrogen atom bonded to the carbon atom of the carbonyl group exhibit good catalytic activity, and that the use of a mixture of 3-Me-$\Delta^4$-THPA and 4-Me-$\Delta^4$-THPA gives a product having a lower melting point.

EXAMPLE 8

Sixty parts of 3-Me-$\Delta^4$-THPA, 40 parts of 4-Me-$\Delta^4$-THPA and a predetermined amount of N,N-dimethylformamide were charged, and reacted under the reaction conditions shown in Table 4. The results are shown in Table 4.

Table 4

| Run No. | 1 | 2 | 3 | 4 |
|---|---|---|---|---|
| Reaction conditions | | | | |
| Amount of the catalyst (parts) | 0.1 | 0.3 | 0.5 | 1 |
| Reaction temperature (°C.) | 200 | 150 | 100 | 100 |
| Reaction time (hours) | 4 | 4 | 10 | 6 |
| Properties | | | | |
| Melting point (°C.) | −20> | −20> | −20> | −20> |
| Gardner color number | 1 | 2 | 2 | 2 |

It is seen from the results that by properly controlling the reaction conditions, it is possible to obtain an isomeric mixture which is liquid even at −20° C.

EXAMPLE 9

Sixty parts of 3-Me-$\Delta^4$-THPA, 40 parts of 4-Me-$\Delta^4$-THPA and 0.5 part of N-butyl-3-methyltetrahydrophthalimide were charged, and reacted in the same way as in Example 5. This reaction afforded a product having a melting point of less than −20° C.

EXAMPLE 10

Sixty parts of 3-Me-$\Delta^4$-THPA, 40 parts of 4-Me-$\Delta^4$-THPA and 0.22 part of n-butylamine were charged, and reacted in the same way as in Example 5. The amount of n-butylamine charged was the theoretical amount required to form 0.5 part of N-butyl-methyltetrahyfrophthalimide in the reaction system.

This reaction afforded a product having a melting point of less than −20° C. It is seen from the results obtained that when the catalyst is added in the form of a primary amine, the same effect is obtained as in the case of adding it in the form of imide.

What we claim is:

1. A process for isomerizing methyl-delta-4-tetrahydrophthalic anhydride without double-bond shift, which comprises heat-treating it at a temperature of 60° to 300° C. for a period of 0.1 to 30 hours in the presence of at least one nitrogen-containing compound selected from the group consisting of (a) a quaternary ammonium compound and (b) a compound having a nitrogen atom bonded to the carbon atom of the carbonyl group.

2. The process of claim 1 wherein the methyl-delta-4-tetrahydrophthalic anhydride consists of 100 to 20% by weight of 3-methyl-delta-4-tetrahydrophthalic anhydride and 0 to 80% by weight of 4-methyl-delta-4-tetrahydrophthalic anhydride.

3. The process of claim 1 wherein the quaternary ammonium compound is a quaternary ammonium salt, a quaternary ammonium hydroxide, an amine salt, an ammonium salt or ammonium hydroxide.

4. The process of claim 1 wherein the nitrogen-containing compound is an amide, imide, carbamic ester, urea, semicarbazide, or a derivative of any of these compounds.

5. A process for preparing an isomeric mixture of methyl-delta-4-tetrahydrophthalic anhydride which is liquid at 20° C., which comprises isomerizing, without double-bond shift, a material comprising 100 to 20% by weight of 3-methyl-delta-4-tetrahydrophthalic anhydride and 0 to 80% by weight of 4-methyl-delta-4-tetrahydrophthalic anhydride at temperatures of 60° to 300° C. for 0.1 to 30 hours in the presence of at least one nitrogen-containing compound selected from the group consisting of (a) a quaternary ammonium compound and (b) a compound having a nitrogen atom bonded to the carbon atom of the carbonyl group.

* * * * *

UNITED STATES PATENT AND TRADEMARK OFFICE
CERTIFICATE OF CORRECTION

PATENT NO. : 4,226,779
DATED : October 7, 1980
INVENTOR(S) : Motoyuki Yamato et al.

It is certified that error appears in the above—identified patent and that said Letters Patent is hereby corrected as shown below:

Column 6, Claim 2, line 44, after "anhydride" insert

-- and an isomeric mixture which is liquid at 20°C. is obtained. --.

*Signed and Sealed this*

*Twenty-eighth* Day of *April 1981*

[SEAL]

*Attest:*

RENE D. TEGTMEYER

*Attesting Officer*   *Acting Commissioner of Patents and Trademarks*